United States Patent
Meyer et al.

(10) Patent No.: US 6,610,826 B1
(45) Date of Patent: Aug. 26, 2003

(54) CYCLOPEPTIDE DERIVATIVES WITH INTEGRIN INHIBITOR PROPERTIES

(75) Inventors: Jörg Meyer, Egelsbach (DE); Alfred Jonczyk, Darmstadt (DE); Berthold Nies, Fränkisch-Crumbach (DE); Horst Kessler, Schwalbach (DE); Dirk Finsinger, München (DE); Martin Kantlehner, Freising (DE)

(73) Assignee: Merck Patent Department (DE)

( * ) Notice: Subject to any disclaimer, the term of this patent is extended or adjusted under 35 U.S.C. 154(b) by 0 days.

(21) Appl. No.: 09/581,575

(22) PCT Filed: Dec. 9, 1998

(86) PCT No.: PCT/EP98/08003

§ 371 (c)(1),
(2), (4) Date: Jun. 15, 2000

(87) PCT Pub. No.: WO99/31126

PCT Pub. Date: Jun. 24, 1999

(30) Foreign Application Priority Data

Dec. 16, 1997 (DE) .......................................... 197 55 800

(51) Int. Cl.⁷ ................................................. C07K 5/10
(52) U.S. Cl. ........................ 530/330; 530/329; 530/331; 530/345; 530/317; 514/11; 514/17; 514/18
(58) Field of Search ................................. 530/330, 331, 530/329, 317, 345; 514/18, 17, 11

(56) References Cited

FOREIGN PATENT DOCUMENTS

| | | |
|---|---|---|
| DE | 195 38 741 | 4/1997 |
| DE | 197 25 368 | 12/1998 |
| EP | 0 844 252 | 5/1998 |

OTHER PUBLICATIONS

Dechantsreiter J Med Chem 42, 3033, 1999.*

Haubner J. Am. Chem. Soc. 118, 7881, 1996.*

D. Delaforge et al.: "Automated solid phase synthesis of cyclic peptides bearings a side–chain tail design for subsequent chemical grafting" *Analytical Biochemistry*, vol. 242, Nov. 1996, pp. 180–186.

D. Delaforge et al., "Automated Solid phase synthesis of cyclic peptides bearing a side–chain tail design for subsequent chemical grafting " *Analytical Biochemistry*, vol. 242, Nov. 1996, pp. 180–186.

* cited by examiner

*Primary Examiner*—Christopher S. F. Low
*Assistant Examiner*—David Lukton
(74) *Attorney, Agent, or Firm*—Millen, White, Zelano & Branigan, P.C.

(57) ABSTRACT

Compounds of the formula I $$R-Q-X \qquad \text{I,}$$

in which R, Q, and X are as defined herein, can be used as integrin inhibitors. In particular, compounds of formula I are suitable for the treatment of disorders caused by implants, defects, inflammations and of osteolytic disorders such as osteoporosis, thrombosis, cardiac infarct and arteriosclerosis. These compounds are also suitable for the acceleration and reinforcement of the integration process of implants and biocompatible surfaces into tissue.

24 Claims, No Drawings

CYCLOPEPTIDE DERIVATIVES WITH INTEGRIN INHIBITOR PROPERTIES

The invention relates to compounds of the formula I

R—Q—X        I in which
R is cyclo-(Arg-Gly-Asp-Z), where Z is bonded in the side chain to Q, or if Q is absent; to X,
Q is absent, or is —[CO—R$^1$—NH—]$_m$, —[NH—R$^1$—CO—]$_m$, —[CO—R$^1$—CO—]$_m$, —(CO—CH$_2$—O—CH$_2$CH$_2$—O—CH$_2$CH$_2$—NH—)$_n$, —(NH—CH$_2$—O—CH$_2$CH$_2$—O—CH$_2$CH$_2$—CO—)$_n$, —(NH—CH$_2$CH$_2$—O—CH$_2$CH$_2$—O—CH$_2$—CO—)$_n$ or —(CO—CH$_2$—O—CH$_2$CH$_2$—O—CH$_2$CH$_2$—NH—)$_n$—[CO—R$^1$—NH—]$_m$,
X is —CO—CH=CH$_2$, —CO—C(CH$_3$)=CH$_2$, —NH—CH=CH$_2$, —NH—C(CH$_3$)=CH$_2$ or —NH—(CH$_2$)$_p$—SR$^{10}$,
Z is in each case independently of one another an amino acid residue or a di- or tripeptide residue, where the amino acids independently of one another are selected from a group consisting of Ala, Asn, Asp, Arg, Cys, Gln, Glu, Gly, His, Homo-Phe, Ile, Leu, Lys, Met, Phe, Phg, Pro, Ser, Thr, Trp, Tyr, Val or M where the amino acids mentioned can also be derivatized, and the amino acid residues are linked to one another in peptide fashion via the α-amino- and α-carboxyl groups, and
where M is always present,
M is NH(R$^8$)—CH(R$^3$)—COOH,
R$^1$ is absent or is R$^2$, R$^9$, R$^2$—R$^9$—R$^2$, or phenylene which is unsubstituted or mono- or disubstituted by R$^5$, where the chain length of R$^5$ is in each case independent of one another,
R$^2$ is alkylene having 1–10 C atoms, where 1 or 2 methylene groups can be replaced by S, —CH=CH— or —C≡C—,
R$^3$ is —R$^5$—R$^4$, —R$^6$—R$^4$ or —R$^7$—R$^4$,
R$^4$ is OH, NH$_2$, SH or COOH,
R$^5$ is alkylene having 1–6 C atoms,
R$^6$ is alkylenephenylene having 7–14 C atoms,
R$^7$ is alkylenephenylalkylene having 8–15 C atoms,
R$^8$ is H, A or alkylenephenyl having 7–12 C atoms,
R$^9$ is cycloalkylene having 3–7 C atoms,
R$^{10}$ is H or an S protective group,
A is alkyl having 1–6 C atoms,
Hal is F, Cl, Br or I
m and n in each case independently of one another are 0, 1, 2 or 3 and
p is 1, 2 or 3,
where, if radicals of optically active amino acids and amino acid derivatives are concerned, both the D and the L forms are included,
and their salts.

Similar cyclic peptide compounds are disclosed in DE 43 10 643 and DE 195 38 741. The compound cyclo-(Art-Gly-Asp-Glu(ε-Ahx-Cys-NH$_2$)-D-Val) is disclosed by D. Delforge et al. in Anal. Biochem. 242, 180–186 (1996).

The invention is based on the object of finding novel compounds having valuable properties, in particular those which can be used for the production of medicaments.

It has been found that the compounds of the formula I and their salts have very valuable pharmacological properties together with good tolerability. They act especially as integrin inhibitors, where they inhibit, in particular, the interactions of the $\alpha_v$-, $\beta_3$- or $\beta_5$-integrin receptors with ligands, such as, for example, the binding of fibrinogen to the $\beta_3$-integrin receptor. The compounds show particular activity in the case of the integrins $\alpha_v\beta_3$, $\alpha_v\beta_5$, $\alpha_{IIb}\beta_3$ and also $\alpha_v\beta_1$, $\alpha_v\beta_6$ and $\alpha_v\beta_8$.

This action can be demonstrated, for example, by the method which is described by J. W. Smith et al. in J. Biol. Chem. 265, 12267–12271 (1990).

The dependence of the origin of angiogenesis on the interaction between vascular integrins and extra-cellular matrix proteins is described by P. C. Brooks, R. A. Clark and D. A. Cheresh in Science 264, 569–71 (1994).

The possibility of the inhibition of this interaction and thus for the initiation of apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I which block the interaction of integrin receptors and ligands, such as, for example, of fibrinogen on the fibrinogen receptor (glycoprotein IIb/IIIa), prevent, as GPIIb/IIIa antagonists, the spread of tumour cells by metastasis. This is confirmed by the following observations: The spread of tumour cells from a local tumour into the vascular system takes place by means of the formation of microaggregates (microthrombi) by interaction of the tumour cells with blood platelets. The tumour cells are screened by the protection in the microaggregates and are not recognized by the cells of the immune system. The microaggregates can collect on vascular walls, whereby further penetration of tumour cells into the tissue is facilitated. Since the formation of the microthrombi is mediated by fibrinogen binding to the fibrinogen receptors on activated blood platelets, the GPIIa/IIIb antagonists can be regarded as efficacious metastasis inhibitors.

The (meth)acrylate radical serves to bond the peptides covalently to biocompatible surfaces of, for example, implants which have free acrylate or methacrylate radicals, such as, for example, poly(methyl methacrylate) moulded articles (bone cements) or acrylate- and methacrylate-containing layers, for example on metal surfaces.

Correspondingly, the thiol radical serves for peptide bonding, for example, to gold surfaces.

The invention therefore relates in particular to the compounds of the formula I for covalent bonding via the functional group of the radical X to biocompatible surfaces.

If X=—NH—(CH$_2$)$_p$—SR$^{10}$, the functional group which bonds to the surface is the SH radical, i.e. if R$^{10}$=H.

The peptides according to the invention now make possible the biofunctionalization of biomaterials, in particular implants for all conceivable organs, by coating thereof, mainly the adhesion of those cell species being stimulated which in each case are intended to accomplish the tissue integration of the appropriate biomaterial. Using such coatings an accelerated and increased integration of various biomaterials/implants with improved long-term stability can be achieved after introduction thereof into the body.

In this connection, reference is made to the second application filed on the same date by the Applicant, in which suitable biomaterials and the coating thereof with the compounds according to the invention are described.

The peptides according to the invention bind selectively to integrins. After immobilization on biocompatible surfaces, e.g. implants, they stimulate the adhesion of cells which carry integrins. After coating of the compounds on the surfaces, those cell species can be selectively stimulated to bind which are also intended to accomplish the implant integration into the natural tissue after implantation. Thus, for example, osteoblasts, osteoclasts and endothelial cells are $\alpha_v$-carrying cell species.

The invention therefore relates to the compounds of the formula I as integrin inhibitors for selective cell enrichment on implants.

After anchorage to a biocompatible surface, the compounds of the formula I can be employed as medicaments in human and veterinary medicine, in particular they can be employed as integrin inhibitors for the treatment of disorders, defects and inflammations caused by implants, such as inadequate and delayed integration of biomaterials and implants, of thrombosis caused by implants, of bone and tooth defects, and also of osteolytic disorders such as osteoporosis, thrombosis, cardiac infarct, arteriosclerosis, in wound healing for assisting the healing process, and also for the acceleration and reinforcement of the integration process of the implant or of the biocompatible surface into the tissue.

The compounds of the formula I can be employed as antimicrobially active substances in operations where biomaterials, implants, catheters or heart pacemakers are used. They have an antiseptic action here. The efficacy of the antimicrobial activity can be demonstrated by the procedure described by P. Valentin-Weigund et al., in Infection and Immunity, 2851–2855 (1988).

The invention thus relates to the compounds of the formula I as integrin inhibitors for the treatment of disorders caused by implants, defects, inflammations and of osteolytic disorders such as osteoporosis, thrombosis, cardiac infarct and arteriosclerosis, and also for the acceleration and reinforcement of the integration process of the implant or of the biocompatible surface into the tissue.

The invention further relates to the use of compounds of the formula I for the production of a medicament for the treatment of disorders caused by implants, defects, inflammations and of osteolytic disorders such as osteoporosis, thrombosis, cardiac infarct and arteriosclerosis, and also for the acceleration and reinforcement of the integration process of the implant or of the biocompatible surface into the tissue.

Appropriate thiol anchor-carrying peptides can be bonded covalently to gold-plated carriers, such as, for example, implants, affinity chromatography media, or microtitre plates.

The invention also relates to the use of the novel compounds of the formula I in affinity chromatography for eluting bound proteins.

In particular, they can be used as integrin ligands for eluting integrins.

The abbreviations of amino acid residues mentioned above and below stand for the residues of the following amino acids:

| Abu | 4-Aminobutyric acid |
| Aha | 6-Aminohexanoic acid, 6-aminocaproic acid |
| Ala | Alanine |
| Asn | Asparagine |
| Asp | Aspartic acid |
| Arg | Arginine |
| Cys | Cysteine |
| Dab | 2,4-Diaminobutyric acid |
| Dap | 2,3-Diaminopropionic acid |
| Gln | Glutamine |
| Glp | Pyroglutamic acid |
| Glu | Glutamic acid |
| Gly | Glycine |
| His | Histidine |
| homo-Phe | Homo-phenylalanine |

-continued

| Ile | Isoleucine |
| Leu | Leucine |
| Lys | Lysine |
| Met | Methionine |
| Nle | Norleucine |
| Orn | Ornithine |
| Phe | Phenylalanine |
| Phg | Phenylglycine |
| 4-Hal-Phe | 4-Halophenylalanine |
| Pmc | 2,2,5,7,8-pentamethylchroman-6-sulfonyl |
| Pro | Proline |
| Ser | Serine |
| Thr | Threonine |
| Trp | Tryptophan |
| Tyr | Tyrosine |
| Val | Valine. |

In addition, the following abbreviations have the meanings given below:

| Ac | Acetyl |
| BOC | tert-Butoxycarbonyl |
| CBZ or Z | Benzyloxycarbonyl |
| DCCI | Dicyclohexylcarbodiimide |
| DMF | Dimethylformamide |
| EDCI | N-Ethyl-N,N'-(dimethylaminopropyl)-carbodiimide |
| Et | Ethyl |
| FCA | Fluoresceincarboxylic acid |
| FITC | Fluorescein isothiocyanate |
| Fmoc | 9-Fluorenylmethoxycarbonyl |
| FTH | Fluoresceinthiourea |
| HOBt | 1-Hydroxybenzotriazole |
| Me | Methyl |
| MBHA | 4-Methylbenzydrylamine |
| Mtr | 4-Methoxy-2,3,6-trimethylphenylsulfonyl |
| HONSu | N-Hydroxysuccinimide |
| OBut | tert-Butyl ester |
| Oct | Octanoyl |
| OMe | Methyl ester |
| OEt | Ethyl ester |
| POA | Phenoxyacetyl |
| Pbf | Pentamethylbenzofuranyl |
| Sal | Salicyloyl |
| Su | Succinyl |
| TFA | Trifluoroacetic acid |
| Trt | Trityl (triphenylmethyl). |

If the abovementioned amino acids can occur in several enantiomeric forms, then all these forms and also their mixtures (e.g. the DL forms) are included above and below, e.g. as a constituent of the compounds of the formula I. In addition, the amino acids can be provided, e.g. as a constituent of compounds of the formula I, with appropriate protective groups known per se. In particular, side chain modifications of the arginine, as have been carried out, for example, in the case of the non-peptide $\alpha_v\beta_3$-antagonists (e.g. by R. Keenan et al., Abstr. Pap. 211th ACS National Meeting (New Orleans, USA) 1996, MEDI 236), can also be employed in the case of the cyclopeptides, such as, for example, benzimidazole derivatives instead of the guanidine group.

So-called prodrug derivatives are also included in the compounds according to the invention, i.e. compounds of the formula I which are modified with, for example, alkyl or acyl groups, sugars or oligopeptides, and which are rapidly cleaved in the body to give the active compounds according to the invention.

These also include biodegradable polymer derivatives of the compounds according to the invention, such as is described, for example, in J. Pharm. 115, 61–67 (1995).

The invention furthermore relates to a process for the preparation of compounds of the formula I according to claim 1 and their salts, characterized in that
(a) for the preparation of compounds of the formula I in which Q is absent, or is —[CO—$R^1$—NH—]$_m$, —(CO—$CH_2$—O—$CH_2CH_2$—O—$CH_2CH_2$—NH—)$_n$ or —(CO—$CH_2$—O—$CH_2CH_2$—O—$CH_2CH_2$—NH—)$_n$—[CO—$R^1$—NH—]$_m$, X is —CO—CH=$CH_2$ or —CO—C($CH_3$)=$CH_2$, and R has the meaning indicated in claim 1, i) a compound of the formula II $$R—H \qquad \text{II}$$

n which

R has the meaning indicated in claim 1, is reacted with a compound of the formula III $$L—Q—X \qquad \text{III}$$

in which

Q is absent, or is —[CO—$R^1$—NH—]$_m$, —(CO—$CH_2$—O—$CH_2CH_2$—O—$CH_2CH_2$—NH—)$_n$ or —(CO—$CH_2$—O—$CH_2CH_2$—O—$CH_2CH_2$—NH—)$_n$—[CO—$R^1$—NH—]$_m$, X is —CO—CH=$CH_2$ or —CO—C($CH_3$)=$CH_2$, and L is Cl, Br, I or a free or reactive functionally modified OH group, or ii) a compound of the formula IV $$R—Q—H \qquad \text{IV}$$

in which

Q is absent, or is —[CO—$R^1$—NH—]$_m$, —(CO—$CH_2$—O—$CH_2CH_2$—O—$CH_2CH_2$—NH—)$_n$ or —(CO—$CH_2$—O—$CH_2CH_2$—O—$CH_2CH_2$—NH—)$_n$[CO—$R^1$—NH—]$_m$, and R has the meaning indicated in claim 1, is reacted with a compound of the formula V $$L—X \qquad \text{V}$$

in which

X is —CO—CH=$CH_2$ or —CO—C($CH_3$)=$CH_2$, and

L is Cl, Br, I or a free or reactive functionally modified OH group, or (b) for the preparation of compounds of the formula I in which Q is absent, or is —[NH—$R^1$—CO—]$_m$, —[CO—$R^1$—CO—]$_m$, —(NH—$CH_2$—O—$CH_2CH_2$—O—$CH_2CH_2$—CO—)$_n$ or —(NH—$CH_2CH_2$—O—$CH_2$—CO—)$_n$, X is —NH—CH=$CH_2$, —NH—C($CH_3$)=$CH_2$ or —NH—$(CH_2)_p$—$SR^{10}$, $R^{10}$ is an S protective group, and R has the meaning indicated in claim 1, i) a compound of the formula VI $$R—L \qquad \text{VI}$$

in which

L is Cl, Br, I or a free or reactive functionally modified OH group, and R has the meaning indicated in claim 1, is reacted with a compound of the formula VII $$H—Q—X \qquad \text{VII}$$

in which

Q is absent, or is —[NH—$R^1$—CO—]$_m$, —(NH—$CH_2$—O—$CH_2CH_2$—O—$CH_2CH_2$—CO—)$_n$ or —(NH—$CH_2CH_2$—O—$CH_2CH_2$—O—$CH_2$—CO—)$_n$, X is —NH—CH=$CH_2$, —NH—C($CH_3$)=$CH_2$ or —NH—$(CH_2)_p$—$SR^{10}$, $R^{10}$ is an S protective group, or ii) a compound of the formula VIII $$R—Q—L \qquad \text{VIII}$$

in which

Q is absent, or is —[NH—$R^1$—CO—]$_m$, —[CO—$R^1$—CO—]$_m$, —(NH—$CH_2$—O—$CH_2CH_2$—O—$CH_2CH_2$—CO—)$_n$ or —(NH—$CH_2CH_2$—O—$CH_2CH_2$—O—$CH_2CH_2$—CO—)$_n$, L is Cl, Br, I or a free or reactive functionally modified OH group, and R has the meaning indicated in claim 1, is reacted with a compound of the formula IX $$H—X \qquad \text{IX}$$

in which

X is —NH—CH=$CH_2$, —NH—C($CH_3$)=$CH_2$ or —NH—$(CH_2)_p$—$SR^{10}$, $R^{10}$ is an S protective group, or (c) in that it is liberated from one of its functional derivatives by treating with a solvolysing or hydrogenolysing agent, and/or in that a basic or acidic compound of the formula I is converted into one of its salts by treating with an acid or base.

Above and below, the radicals R, Q, X and L have the meanings indicated in the formulae I, II, III, IV, V, VI, VII, VIII and IX, if not expressly indicated otherwise.

In the above formulae, alkyl is preferably methyl, ethyl, propyl, isopropyl, butyl, isobutyl, sec-butyl or tert-butyl, additionally also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

$R^1$ is $R^2$, $R^9$, $R^2$—$R^9$—$R^2$, phenylene which is unsubstituted or mono- or disubstituted by $R^5$, where the chain length of $R^5$ is in each case independent of one another, or $R^1$ is absent; in particular $R^1$ is alkylene having 1–10 C atoms.

Alkylene is preferably methylene, ethylene, butylene, pentylene or hexylene, additionally heptylene, octylene, nonylene or decylene.

Alylenephenyl is preferably benzyl or phenethyl. Alkylenephenylalkylene is preferably 4-methylenebenzyl or 4-ethylenebenzyl.

Q is preferably, for example, the 6-aminohexanoic acid (6-aminocaproic acid) radical, the succinyl radical, the —(CO—$CH_2$—O—$CH_2CH_2$—O—$CH_2CH_2$—NH)—, the —(CO—$CH_2$—O—$CH_2CH_2$—O—$CH_2CH_2$—NH—) CO—$(CH_2)_5$—NH—, the —(CO—$(CH_2)_5$—NH)$_2$— radical or the —(CO—$CH_2$—O—$CH_2CH_2$—O—$CH_2CH_2$—NH—)$_2$CO—$(CH_2)_5$—NH— radical.

M is preferably Dap, Ser, Cys, Asp, D-Asp, Dab, homoserine, homocysteine, Glu, D-Glu, Thr, Orn, Lys, D-Lys, 4-aminomethyl-Phe or 4-aminomethyl-D-Phe.

The amino acids and amino acid residues mentioned in the meanings for Z can also be derivatized, the N-methyl, N-ethyl, N-propyl, N-benzyl and $C_\alpha$-methyl derivatives being preferred. Derivatives of Asp and Glu, in particular the methyl, ethyl, propyl, butyl, tert-butyl, neopentyl or benzyl esters of the side chain carboxyl groups are furthermore preferred, additionally also derivatives of Arg which can be substituted on the —NH—C(=NH)—NH$_2$— group by an acetyl, benzoyl, methoxycarbonyl or ethoxycarbonyl radical.

Z is preferably M, furthermore preferably homo-Phe-M, phenylglycine, D-Phe-M, D-Trp-M, D-Tyr-M, D-Phe-Lys, D-Phe-D-Lys, D-Trp-Lys, D-Trp-D-Lys, D-Tyr-Lys, D-Tyr-D-Lys, D-Phe-Orn, D-Phe-Dab, D-Phe-Dap, D-Phe-D-Orn, D-Phe-D-Dab, D-Phe-D-Dap, D-Phe-4-aminomethyl-Phe, D-Phe-4-aminomethyl-D-Phe, D-Trp-4-aminomethyl-Phe, D-Trp-4-aminomethyl-D-Phe, D-Tyr-4-aminomethyl-Phe, D-Tyr-4-aminomethyl-D-Phe, D-Phe-Asp, D-Phe-D-Asp, D-Trp-Asp, D-Trp-D-Asp, D-Tyr-Asp, D-Tyr-D-Asp, D-Phe-Cys, D-Phe-D-Cys, D-Trp-Cys, D-Trp-D-Cys, D-Tyr-Cys, D-Tyr-D-Cys, Phe-D-Lys, Trp-D-Lys, Tyr-D-Lys, Phe-Orn, Phe-Dab, Phe-Dap, Trp-Orn, Trp-Dab, Trp-Dap, Tyr-Orn, Tyr-Dab, Tyr-Dap, Phe-4-aminomethyl-D-Phe, Trp-4-aminomethyl-D-Phe, Tyr-4-aminomethyl-D-Phe, Phe-D-Asp, Trp-D-Asp, Tyr-D-Asp, Phe-D-Cys, Trp-D-Cys, Tyr-D-Cys, Phg-M, D-Phe-Lys-Gly, D-Phe-M-Gly, D-Trp-Lys-Gly, D-Trp-M-Gly, D-Tyr-Lys-Gly, D-Tyr-M-Gly, D-Phe-Val-Lys, D-Phe-Gly-Lys, D-Phe-Ala-Lys, D-Phe-Ile-Lys, D-Phe-Leu-Lys, D-Trp-Val-Lys, D-Trp-Gly-Lys, D-Trp-Ala-Lys, D-Trp-Ile-Lys, D-Trp-Leu-Lys, D-Tyr-Val-Lys, D-Tyr-Gly-Lys, D-Tyr-Ala-Lys, D-Tyr-Ile-Lys, D-Tyr-Leu-Lys.

The radical —$R^6$—$R^4$ is preferably 2-, 3- or 4-hydroxybenzyl, 2-, 3- or 4-aminobenzyl, 2-, 3- or 4-mercaptobenzyl, 2-, 3- or 4-carboxybenzyl, additionally preferably 2-, 3- or 4-hydroxyphenethyl, 2-, 3- or 4-aminophenethyl, 2-, 3- or 4-mercaptophenethyl, 2-, 3- or 4-carboxyphenethyl.

Cycloalkylene is preferably cyclopropylene, 1,2- or 1,3-cyclobutylene, 1,2- or 1,3-cyclopentylene, 1,2-, 1,3- or 1,4-cyclohexylene, additionally 1,2-, 1,3- or 1,4-cycloheptylene.

$R^{10}$ is H or an S protective group, such as, for example, trityl.

An amino protective group is preferably acetyl, propionyl, butyryl, phenylacetyl, benzoyl, toluyl, POA, methoxycarbonyl, ethoxycarboryl, 2,2,2-trichloroethoxycarbonyl, BOC, 2-iodoethoxycarbonyl, CBZ ("carbobenzoxy"), 4-methoxybenzyloxycarbonyl, FMOC, Mtr, benzyl, Pbf or Pmc.

Hal is preferably F, Cl or Br, but also I.

The compounds of the formula I can have one or more chiral centres and therefore occur in various stereo-isomeric forms. The formula I includes all these forms.

Accordingly, the invention relates in particular to those compounds of the formula I in which at least one of the radicals mentioned has one of the preferred meanings indicated above. Some preferred groups of compounds can be expressed by the following subformulae Ia to If, which correspond to the formula I and in which the radicals not designated in greater detail have the meaning indicated in the formula I, but in which in a)
Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly;

in b)
Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly, X is —CO—CH=CH$_2$, —NH—CH=CH$_2$, or —NH—(CH$_2$)$_p$—SH;

in c)
Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly, X is —CO—CH=CH$_2$ or —NH—(CH$_2$)$_p$—SH, in d)
Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly, X is —CO—CH=CH$_2$, —NH—CH=CH$_2$ or —NH—(CH$_2$)$_p$—SH, $R^1$ is $R^2$, in e)
R is cyclo-(Arg-Gly-Asp-D-Phe-M) or D-Phe-Lys-Gly, X is —CO—CH=CH$_2$, —NH—CH=CH$_2$ or —NH—(CH$_2$)$_p$—SH, in f)
R is cyclo-(Arg-Gly-Asp-D-Phe-M) or D-Phe-Lys-Gly, Q is —CO—(CH$_2$)$_5$—NH—, —CO—(CH$_2$)$_2$—CO—, —CO—CH$_2$—O—CH$_2$CH$_2$—O—CH$_2$CH$_2$—NH—, —(CO—CH$_2$—O—CH$_2$CH$_2$—O—CH$_2$CH$_2$—NH—)$_2$—CO—(CH$_2$)$_5$—NH—, —(CO—CH$_2$—O—CH$_2$CH$_2$—O—CH$_2$CH$_2$—NH—)$_1$—CO—(CH$_2$)$_5$—NH— or —(CO—(CH$_2$)$_5$—NH)$_2$—, X is —CO—CH=CH$_2$, —NH—CH=CH$_2$ or —NH—(CH$_2$)$_p$—SH, $R^1$ is $R^2$.

The compounds of the formula I and also the starting substances for their preparation are otherwise prepared by methods known per se, such as are described in the literature (e.g. in the standard works such as Houben-Weyl, Methoden der Organischen Chemie [Methods of Organic Chemistry], Georg-Thieme-Verlag, Stuttgart), namely under reaction conditions which are known and suitable for the reactions mentioned. In this case use can also be made of variants which are known per se, but not mentioned here in greater detail.

If desired, the starting substances can also be formed in situ in such a way that they are not isolated from the reaction mixture, but immediately reacted further to give the compounds of the formula I.

Compounds of the formula I can preferably be obtained by reacting compounds of the formula II with compounds of the formula III.

As a rule, the compounds of the formulae II and III are known. If they are not known, they can be prepared by methods known per se.

In the compounds of the formula III, the radical L is preferably a preactivated carboxylic acid, preferably a carboxylic acid halide, symmetrical or mixed anhydride or an active ester. Radicals of this type for the activation of the carboxyl group in typical acylation reactions are described in the literature (e.g. in the standard works such as Houben-Weyl, Methoden der Organischen Chemie [Methods of Organic Chemistry], Georg-Thieme-Verlag, Stuttgart).

Activated esters are expediently formed in situ, e.g. by addition of HOBt or N-hydroxysuccinimide.

L is preferably H, F, Cl, Br or —ON-succinimide.

As a rule, the reaction is carried out in an inert solvent, in the presence of an acid-binding agent, preferably of an organic base such as DIPEA, triethylamine, dimethylaniline, pyridine or quinoline or of an excess of the carboxyl component of the formula III.

The addition of an alkali metal or alkaline earth metal hydroxide, carbonate or bicarbonate or of another salt of a weak acid of the alkali metals or alkaline earth metals, preferably of potassium, sodium, calcium or caesium, may be favourable.

Depending on the conditions used, the reaction time is between a few minutes and 14 days, the reaction temperature between approximately −30° and 140°, normally between −10° and 90°, in particular between approximately 0° and approximately 70°.

Suitable inert solvents are, for example, hydrocarbons such as hexane, petroleum ether, benzene, toluene or xylene; chlorinated hydrocarbons such as trichloro-ethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, N-methylpyrrolidone, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, water or mixtures of the solvents mentioned.

Compounds of the formula I can furthermore be obtained by reacting compounds of the formula IV with compounds of the formula V.

As a rule, the starting compounds of the formulae IV and V are known. If they are not known, they can be prepared by methods known per se.

In the compounds of the formula V, the radical L is preferably a preactivated carboxylic acid, preferably a carboxylic acid halide, symmetrical or mixed anhydride or an active ester. Radicals of this type for the activation of the carboxyl group in typical acylation reactions are described in the literature (e.g. in the standard works such as Houben-Weyl, Methoden der Organischen Chemie [Methods of Organic Chemistry], Georg-Thieme-Verlag, Stuttgart).

L is preferably F, Cl, Br or —ON-succinimide.

The reaction of the compounds of the formula IV with compounds of the formula V is carried out under the same conditions, concerning the reaction time, temperature and solvent, as is described for the reaction of the compounds of the formula II with compounds of the formula III.

Compounds of the formula I can furthermore be obtained by reacting compounds of the formula VI with compounds of the formula VII.

As a rule, the starting compounds of the formulae VI and VII are known. If they are not known, they can be prepared by methods known per se.

In the compounds of the formula VI the radical L is preferably a preactivated carboxylic acid, preferably a carboxylic acid halide, symmetrical or mixed anhydride or an active ester. Radicals of this type for the activation of the carboxyl group in typical acylation reactions are described in the literature (e.g. in the standard works such as Houben-Weyl, Methoden der Organischen Chemie [Methods of Organic Chemistry], Georg-Thieme-Verlag, Stuttgart).

L is preferably F, Cl, Br or —ON-succinimide.

The reaction of the compounds of the formula VI with compounds of the formula VII is carried out under the same conditions, concerning the reaction time, temperature and solvent, as is described for the reaction of the compounds of the formula II with compounds of the formula III.

Compounds of the formula I can furthermore be obtained by reacting compounds of the formula VIII with compounds of the formula IX.

As a rule, the starting compounds of the formulae VIII and IX are known. If they are not known, they can be prepared by methods known per se.

In the compounds of the formula VIII, the radical L is preferably a preactivated carboxylic acid, preferably a carboxylic acid halide, symmetrical or mixed anhydride or an active ester. Radicals of this type for the activation of the carboxyl group in typical acylation reactions are described in the literature (e.g. in the standard works such as Houben-Weyl, Methoden der Organischen Chemie [Methods of Organic Chemistry], Georg-Thieme-Verlag, Stuttgart).

L is preferably F, Cl, Br or —ON-succinimide.

The reaction of the compounds of the formula VIII with compounds of the formula IX is carried out under the same conditions, concerning the reaction time, temperature and solvent, as is described for the reaction of the compounds of the formula II with compounds of the formula III.

Cyclic compounds of the formula II can be prepared by cyclization of the linear compounds, such as described, for example, in DE 43 10 643, in Houben-Weyl, l.c., Volume 15/II, pages 1 to 806 (1974) or by S. Zimmer, E. Hoffmann, G. Jung and H. Kessler, Liebig's Ann. Chem. 1993, 497–501.

The linear peptides can be synthesized, for example, according to R. B. Merrifield, Angew. Chemie 1985, 97, 801–812.

Open-chain linear compounds, such as, for example, compounds of the formula III can otherwise be prepared by customary methods of amino acid and peptide synthesis, e.g. also by the solid-phase synthesis according to Merrifield (see also, for example, B. F. Gysin and R. B. Merrifield, J. Am. Chem. Soc. 94, 3012 ff. (1972)).

The compounds of the formula I can furthermore be obtained by liberating them from their functional derivatives by solvolysis, in particular hydrolysis, or by hydrogenolysis.

Preferred starting substances for the solvolysis or hydrogenolysis are those which, instead of one or more free amino and/or hydroxyl groups, contain corresponding protected amino and/or hydroxyl groups, preferably those, which instead of an H atom which is bonded to an N atom, carry an amino protective group, e.g. those which correspond to the formula I, but instead of an $NH_2$ group contain an NHR' group (in which R' is an amino protective group, e.g. BOC or CBZ).

Starting substances are furthermore preferred which, instead of the H atom of a hydroxyl group, carry a hydroxyl protective group, e.g. those which correspond to the formula I, but instead of a hydroxyphenyl group contain an R"O—phenyl group (in which R" is a hydroxy protective group).

A number of—identical or different—protected amino and/or hydroxyl groups can also be present in the molecule of the starting substance. If the protective groups present are different from one another, in many cases they can be removed selectively.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the protective groups are removed after the desired reaction (or reaction sequence), their nature and size is otherwise uncritical; preferably, however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl, FMOC; arylsulfonyl such as Mtr, Pbf or Pmc. Preferred amino protective groups are BOC and Mtr, additionally CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other positions in the molecule. Typical groups of this type are the abovementioned unsubstituted or substituted aryl, aralkyl or acyl groups and additionally also alkyl groups. The nature and size of the hydroxyl protective groups is not critical, since they are removed again after the desired chemical reaction or reaction sequence; groups containing 1–20, in particular 1–10, C atoms are preferred. Examples of hydroxyl protective groups are, inter alia, benzyl, p-nitrobenzyl, p-toluenesulfonyl, tert-butyl and acetyl, benzyl and tert-butyl being particularly preferred. The COOH groups in aspartic acid and glutamic acid are preferably protected in the form of their tert-butyl esters (e.g. Asp(OBut)).

The liberation of the compounds of the formula I from their functional derivatives is carried out—depending on the protective group used—, for example using strong acids, expediently using TFA or perchloric acid but also using other strong inorganic acids such as hydrochloric acid or sulfuric acid, strong organic carboxyl ic acids such as trichloroacetic acid or sulfonic acids such as benzene- or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, additionally also alcohols such as methanol, ethanol or isopropanol, and also water. Mixtures of the abovementioned solvents are additionally suitable. TFA is preferably used in a n excess without addition of a further solvent , perchloric acid in the form of a mixture of acetic acid and 70% perchloric acid in the ratio 9:1. The reaction temperatures for the cleavage are expediently between approximately 0 and approximately 50°, the reaction is preferably carried out between 15 and 30°(room temperature).

The groups BOC, OBut, Pbf, Pmc and Mtr can be removed, for example, preferably using TFA in dichloromethane or using approximately 3 to 5 N HCl in dioxane at 15–30°, the FMOC group using an approximately 5 to 50% solution of dimethylamine, diethylamine or piperidine in DMF at 15–30°.

The trityl group is employed for the protection of the amino acids hisitidine, asparagine, glutamine and cysteine. Removal is carried out, depending on the desired final product, using TFA/10% thiophenol, the trityl group being removed from all the abovementioned amino acids, when using TFA/anisole or TFA/thioanisole the trityl group only being removed from His, Asn and Gln, compared to which that on the Cys side chain remains. The Pbf (pentamethylbenzofuranyl) group is employed for the protection of Arg. Removal is carried out, for example, using TFA in dichloromethane.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents in this case are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° and 1–10 bar. Hydrogenolysis of the CBZ group is readily carried out, for example, on 5 to 10% Pd/C in methanol or using ammonium formate (instead of hydrogen) on Pd/C in methanol/DMF at 20–30°.

A base of the formula I can be converted into the associated acid addition salt using an acid, for example by reaction of equivalent amounts of the base and of the acid in an inert solvent such as ethanol and subsequent evaporation. Possible acids for this reaction are in particular those which give physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, additionally organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluene-sulfonic acid, naphthalenemono- and -disulfonic acids, and laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Suitable salts in this case are in particular the sodium, potassium, magnesium, calcium and ammonium salts, additionally substituted ammonium salts, e.g. the dimethyl-, diethyl- or diisopropylammonium salts, monoethanol-, diethanol- or diisopropylammonium salts, cyclohexyl- or dicyclohexylammonium salts, dibenzylethylenediammonium salts, furthermore, for example, salts with arginine or lysine.

Above and below, all temperatures are indicated in °C. In the following examples "customary working up" means: if necessary, water is added, the mixture is adjusted, if necessary, depending on the constitution of the final product to a pH of between 2 and 10 and extracted with ethyl acetate or dichloromethane, the organic phase is separated off, dried over sodium sulfate and evaporated, and the residue is purified by chromatography on silica gel and/or by crystallization. $R_f$ values on silica gel: eluent: ethyl acetate/methanol 9:1.

RT=Retention time (minutes) on HPLC in the following systems:

[A]
Column: YMC ODS A RP $5C_{18}$, 250×4.6 mm
Eluent A: 0.1% TFA in water
Eluent B: 0.1% TFA in acetonitrile Flow rate: 1 ml/min
Gradient: 0–50% B/30 min.
[B] as [A];
Gradient: 5–50% B/30 min.
[C] as [A];
Gradient: 10–50% B/30 min.
Mass spectrometry (MS):

EI (electron impact ionization) M+
FAB (Fast Atom Bombardment) (M+H)+
ESI (electrospray ionization) (M+H)+

DMPP resin stands for 4-(2',4'-dimethoxyphenylhydroxymethyl)phenoxy resin, which allows, for example, the synthesis of side chain-protected peptides; TCP resin denotes trityl chloride polystyrene resin.

EXAMPLE 1 a) 0.2 mmol of succinic anhydride is added to a solution of 0.1 mmol of cyclo-(Arg(Pbf)-Gly-Asp(OBut)-D-Phe-Lys) ("A") [obtainable by cyclization of H-Asp(OBut)-D-Phe-Lys(Z)-Arg(Pbf)-Gly-OH to cyclo-(Arg(Pbf)-Gly-Asp(OBut)-D-Phe-Lys(Z)) and selective removal of the Z group by hydrogenolysis] in 5 ml of DMF.
The mixture is stirred at room temperature for 5 hours and cyclo-(Arg(Pbf)-Gly-Asp(OBut)-D-Phe-Lys(N$^\epsilon$-Su)) ("B") is obtained after customary working up.

b) 1 equivalent of cysteamine hydrochloride and 1 equivalent of triphenylmethanol are dissolved in glacial acetic acid at 60° and treated with stirring with 1.1 equivalents of BF$_3$ etherate. The mixture is stirred for one hour and worked up in the customary manner and Trt-cysteamine hydrochloride ("C") is obtained.

By reaction of "B" with "C" in dichloromethane with the addition of EDCI hydrochloride, cyclo-(Arg(Pbf)-Gly-Asp(OBut)-D-Phe-Lys(N$^\epsilon$—CO—CH$_2$CH$_2$CO—NH—CH$_2$CH$_2$—S-Trt)) is obtained after customary working up.

After removal of the protective groups cyclo-(Arg-Gly-Asp-D-Phe-Lys(N$^\epsilon$—CO—CH$_2$CH$_2$CO—NH—CH$_2$CH$_2$—SH)) is obtained; RT [B] 18.3; FAB 763.

Analogously, by reaction of "C" with cyclo-(Arg(Pbf)-Gly-Asp (OBut)-D-Phe-Lys(N$^\epsilon$—Su)-Gly) and removal of the protective groups the compound cyclo-(Arg-Gly-Asp-D-Phe-Lys(N$^\epsilon$—CO—CH$_2$CH$_2$CO—NH—CH$_2$CH$_2$—SH)-Gly) is obtained.

EXAMPLE 2 a) 1.2 equivalents of acryolyl chloride are added at 0° to a suspension of 10 mmol of 6-aminohexanoic acid and 1.8 equivalents of calcium hydroxide in water. The mixture is filtered and 6-acrylamidohexanoic acid ("D") is obtained after customary working up.

b) A solution of 10 mmol of "DE" and 1 equivalent of N-hydroxysuccinimide in 50 ml of dichloromethane is treated at 0° with 1.2 equivalents of EDCI hydrochloride and stirred for 1 hour. 10 μl of glacial acetic acid are added, the mixture is worked up in the customary manner and HOBT 6-acrylamidohexanoate ("E") is obtained.

c) By reaction of "A" with "E" in DMF, cyclo-(Arg(Pbf)-Gly-Asp(OBut)-D-Phe-Lys(N$^\epsilon$—CO—(CH$_2$)$_5$—NH—CO—CH=CH$_2$)) is obtained after customary working up. After removal of the protective groups cyclo-(Arg-Gly-Asp-D-Phe-Lys(N$^\epsilon$—CO—(CH$_2$)$_5$—NH—CO—CH=CH$_2$)) is obtained; RT [A] 22.8; ESI 771.

The compound cyclo-(Arg-Gly-Asp-D-Phe-Lys(N$^\epsilon$—CO—(CH$_2$)$_5$—NH—CO—CH=CH$_2$)-Gly) is obtained analogously.

EXAMPLE 3 a) 2 mmol of "E", dissolved in ethanol/chloroform, are added at 0° to a solution of 10 mmol of 6-aminohexanoic acid in aqueous sodium phosphate buffer (pH 8). The mixture is filtered and 6-(6-acrylamidohexanoylamido)hexanoic acid ("F")

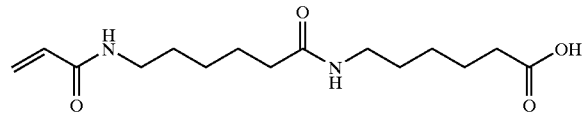

is obtained after customary working up.

b) By reaction of "A" with "F" in DMF with addition of EDCI hydrochloride, cyclo-(Arg(Pbf)-Gly-Asp(OBut)-D-Phe-Lys (N$^\epsilon$—CO—(CH$_2$)$_5$—NH—CO—(CH$_2$)$_5$—NH—CO—CH=CH$_2$)) is obtained after customary working up.

After removal of the protective groups cyclo-(Arg-Gly-Asp-D-Phe-Lys(N$^\epsilon$—CO—(CH$_2$)$_5$—NH—CO—(CH$_2$)$_5$—NH—CO—CH=CH$_2$)) is obtained; RT [C] 23.5; ESI 884.

The compound cyclo-(Arg-Gly-Asp-D-Phe-Lys(N$^\epsilon$—CO—(CH$_2$)$_5$—NH—CO—(CH$_2$)$_5$—NH—CO—CH=CH$_2$)-Gly) is obtained analogously.

EXAMPLE 4 a) By coupling of 6-acrylamidohexanoic acid to [2-(2-aminoethoxy)ethoxy]acetic acid-TCP resin with addition of HOBt and TBTU in NMP {2-[2-(6-acrylamidohexanoylamido)ethoxy]ethoxy}acetic acid-DMPP resin is obtained.

The resin is washed with dichloromethane/acetic acid/trifluoroethanol (6:3:1) and {2-[2-(6-acrylamidohexanoylamido) ethoxy]ethoxy}acetic acid ("G") is obtained.

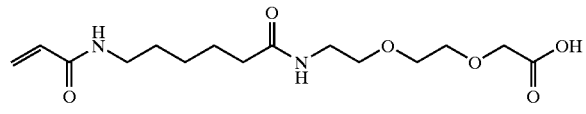

b) By reaction of "G" with "A" in DMF with addition of EDClxHCl, the compound cyclo-(Arg(Pbf)-Gly-Asp(OBut)-D-Phe-Lys(N$^\epsilon$—CO—CH$_2$—O—CH$_2$CH$_2$—O—CH$_2$CH$_2$—NH—CO—(CH$_2$)$_5$—NH—CO—CH=CH$_2$)) is obtained.

After removal of the protective groups cyclo-(Arg-Gly-Asp-D-Phe-Lys(N$^\epsilon$—CO—CH$_2$—O—CH$_2$CH$_2$—O—CH$_2$CH$_2$—NH—CO—(CH$_2$)$_5$—NH—CO—CH=CH$_2$)) is obtained; RT [C] 22.5; ESI 916.

The compound cyclo-(Arg-Gly-Asp-D-Phe-Lys(N$^\epsilon$—CO—CH$_2$—O—CH$_2$CH$_2$—O—CH$_2$CH$_2$—NH—CO—(CH$_2$)$_5$—NH—CO—CH=CH$_2$)-Gly) is obtained analogously.

Analogously, by reaction of {2-[2-(2-{2-[2-(6-acrylamidohexanoylamido)ethoxy]-ethoxy]acetylamido) ethoxy]ethoxy}acetic acid

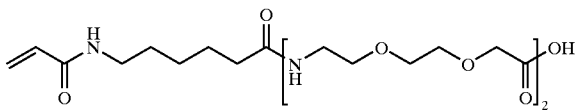

with "A" the compound cyclo-(Arg(Pbf)-Gly-Asp(OBut)-D-Phe-Lys(N$^\epsilon$—(CO—CH$_2$—O—CH$_2$CH$_2$—O—CH$_2$CH$_2$—NH)$_2$—CO—(CH$_2$)$_5$—NH—CO—CH=CH$_2$)) is obtained. After removal of the protective groups cyclo-(Arg-Gly-Asp-D-Phe-Lys(N$_\epsilon$—(CO—CH$_2$—O—CH$_2$CH$_2$—O—CH$_2$CH$_2$—NH)$_2$—CO—(CH$_2$)$_5$—NH—CO—CH=CH$_2$)) is obtained; RT [C] 22.75; ESI 1061.

Cyclo-(Arg-Gly-Asp-D-Phe-Lys(N$^\epsilon$—(CO—CH$_2$—O—CH$_2$CH$_2$—O—CH$_2$CH$_2$—NH)$_2$—CO—(CH$_2$)$_5$—NH—CO—CH=CH$_2$)-Gly) is obtained analogously.

EXAMPLE 5

Analogously to Example 1, by reaction of the ("G")-cyclopeptides below cyclo-(Arg(Pbf)-Gly-Asp(OBut)-D-Phe-Val-Lys)
cyclo-(Arg(Pbf)-Gly-Asp(OBut)D-Trp-Lys)
cyclo-(Arg(Pbf)-Gly-Asp(OBut)-D-Tyr-Lys)
cyclo-(Arg(Pbf)-Gly-Asp(OBut)-D-Phe-D-Lys)
cyclo-(Arg(Pbf)-Gly-Asp(OBut)-D-Phe-Cys)
cyclo-(Arg(Pbf)-Gly-Asp(OBut)-D-Phe-Dab)
cyclo-(Arg(Pbf)-Gly-Asp(OBut)-D-Trp-D-Cys)
cyclo-(Arg(Pbf)-Gly-Asp(OBut)-D-Tyr-D-Cys)
cyclo-(Arg(Pbf)-Gly-Asp(OBut)-Phe-D-Lys)
cyclo-(Arg(Pbf)-Gly-Asp(OBut)-Trp-D-Lys)
cyclo-(Arg(Pbf)-Gly-Asp(OBut)-Tyr-D-Lys)
cyclo-(Arg(Pbf)-Gly-Asp(OBut)-Phe-D-Cys)
cyclo-(Arg(Pbf)-Gly-Asp(OBut)-Phe-Dab)
cyclo-(Arg(Pbf)-Gly-Asp(OBut)-Trp-D-Cys)
cyclo-(Arg(Pbf)-Gly-Asp(OBut)-Tyr-D-Cys)
cyclo-(Arg(Pbf)-Gly-Asp(OBut)-D-Trp-Orn)
cyclo-(Arg(Pbf)-Gly-Asp(OBut)-D-Tyr-Orn)
cyclo-(Arg(Pbf)-Gly-Asp(OBut)-D-Phe-Orn)
cyclo-(Arg(Pbf)-Gly-Asp(OBut)-D-Trp-D-Orn)
cyclo-(Arg(Pbf)-Gly-Asp(OBut)-D-Tyr-D-Orn)
cyclo-(Arg(Pbf)-Gly-Asp(OBut)-D-Phe-D-Orn)
cyclo-(Arg(Pbf-Gly-Asp(OBut)-D-Trp-Dab)
cyclo-(Arg(Pbf)-Gly-Asp(OBut)-D-Tyr-Dab)
cyclo-(Arg(Pbf)-Gly-Asp(OBut)-D-Trp-Dap)
cyclo-(Arg(Pbf)-Gly-Asp(OBut)-D-Tyr-Dap)
cyclo-(Arg(Pbf)-Gly-Asp(OBut)-D-Phe-Dap)
cyclo-(Arg(Pbf-Gly-Asp(OBut)-D-Trp-D-Dap)
cyclo-(Arg(Pbf-Gly-Asp(OBut)-D-Tyr-D-Dap)
cyclo-(Arg(Pbf)-Gly-Asp(OBut)-D-Phe-D-Dap)
with
  a) succinic anhydride, b) "C" and c) removal of the protective groups the following compounds are obtained cyclo-(Arg-Gly-Asp-D-Phe-Val-Lys(N$^\epsilon$—CO—CH$_2$CH$_2$CO—NH—CH$_2$CH$_2$—SH))
cyclo-Arg-Gly-Asp-D-Trp-Lys(N$^\epsilon$—CO—CH$_2$CH$_2$CO—NH—CH$_2$CH$_2$—SH))
cyclo-(Arg-Gly-Asp-D-Tyr-Lys(N$^\epsilon$—CO—CH$_2$CH$_2$CO—NH—CH$_2$CH$_2$—SH))
cyclo-(Arg-Gly-Asp-D-Phe-D-Lys(N$^\epsilon$—CO—CH$_2$CH$_2$CO—NH—CH$_2$CH$_2$—SH))
cyclo-Arg-Gly-Asp-D-Phe-Cys(S—CO—CH$_2$CH$_2$CO—NH—CH$_2$CH$_2$—SH))
cyclo-(Arg-Gly-Asp-D-Phe-Dab(N$^\gamma$—CO—CH$_2$Ch$_2$CO—NH—CH$_2$CH$_2$—SH))
cyclo-Arg-Gly-Asp-D-Trp-D-Cys(S—CO—CH$_2$CH$_2$CO—NH—CH$_2$CH$_2$—SH))
cyclo-(Arg-Gly-Asp-D-Tyr-D-Cys(S—CO—CH$_2$CH$_2$CO—NH—CH$_2$CH$_2$—SH))
cyclo-(Arg-Gly-Asp-Phe-D-Lys(N$^\epsilon$—CO—CH$_2$CH$_2$CO—NH—CH$_2$CH$_2$—SH))
cyclo-(Arg-Gly-Asp-Trp-D-Lys(N$^\epsilon$—CO—CH$_2$CH$_2$CO—NH—CH$_2$CH$_2$—SH))
cyclo-(Arg-Gly-Asp-Tyr-D-Lys(N$^\epsilon$—CO—CH$_2$CH$_2$CO—NH—CH$_2$CH$_2$—SH))
cyclo-(Arg-Gly-Asp-Phe-D-Cys(S—CO—CH$_2$CH$_2$CO—NH—CH$_2$CH$_2$—SH))
cyclo-(Arg-Gly-Asp-Phe-Dab(N$^\gamma$—CO—CH$_2$CH$_2$CO—NH—CH$_2$CH$_2$—SH))
cyclo-(Arg-Gly-Asp-Trp-D-Cys(S—CO—CH$_2$CH$_2$CO—NH—CH$_2$CH$_2$—SH))
cyclo-(Arg-Gly-Asp-Tyr-D-Cys(S—CO—CH$_2$CH$_2$CO—NH—CH$_2$CH$_2$—SH))
cyclo-(Arg-Gly-Asp-D-Trp-Orn(N$^\delta$—CO—CH$_2$CH$_2$CO—NH—CH$_2$CH$_2$—SH))
cyclo-(Arg-Gly-Asp-D-Tyr-Orn(N$^\delta$—CO—CH$_2$CH$_2$CO—NH—CH$_2$CH$_2$—SH))
cyclo-(Arg-Gly-Asp-D-Phe-Orn(N$^\delta$—CO—CH$_2$CH$_2$CO—NH—CH$_2$CH$_2$—SH))
cyclo-(Arg-Gly-Asp-D-Trp-D-Orn(N$^\delta$—CO—CH$_2$CH$_2$CO—NH—CH$_2$CH$_2$—SH))
cyclo-(Arg-Gly-Asp-D-Tyr-D-Orn(N$^\delta$—CO—CH$_2$CH$_2$CO—NH—CH$_2$CH$_2$—SH))
cyclo-(Arg -Gly-Asp-D-Phe-D-Orn(N$^\delta$—CO—CH$_2$CH$_2$CO—NH—CH$_2$CH$_2$—SH))
cyclo-(Arg-Gly-Asp-D-Trp-Dab(N$^\delta$—CO—CH$_2$CH$_2$CO—NH—CH$_2$CH$_2$—SH))
cyclo-(Arg-Gly-Asp-D-Tyr-Dab(N$^\delta$—CO—CH$_2$CH$_2$CO—NH—CH$_2$CH$_2$—SH))
cyclo-(Arg-Gly-Asp-D-Trp-Dap(N$^\beta$—CO—CH$_2$CH$_2$CO—NH—CH$_2$CH$_2$—SH))
cyclo-(Arg-Gly-Asp-D-Tyr-Dap(N$^\beta$—CO—CH$_2$CH$_2$CO—NH—CH$_2$CH$_2$—SH))
cyclo-(Arg-Gly-Asp-D-Phe-Dap(N$^\beta$—CO—CH$_2$CH$_2$CO—NH—CH$_2$CH$_2$—SH))
cyclo-(Arg-Gly-Asp-D-Trp-D-Dap(N$^\beta$—CO—CH$_2$CH$_2$CO—NH—CH$_2$CH$_2$—SH))
cyclo-(Arg-Gly-Asp-D-Tyr-D-Dap(N$^\beta$—CO—CH$_2$CH$_2$CO—NH—CH$_2$CH$_2$—SH))
cyclo-(Arg-Gly-Asp-D-Phe-D-Dap(N$^\beta$—CO—CH$_2$CH$_2$CO—NH—CH$_2$CH$_2$—SH)).

Analogously to Example 2, by reaction of the "G" cyclopeptides with
  a) "E" and b) removal of the protective groups the following compounds are obtained cyclo-(Arg-Gly-Asp-D-Phe-Val-Lys(N$^\epsilon$—CO—(CH$_2$)$_5$—NH—CO—CH=CH$_2$))
cyclo-(Arg-Gly-Asp-D-Trp-Lys(N$^\epsilon$—CO—(CH$_2$)$_5$—NH—CO—CH=CH$_2$))
cyclo-(Arg-Gly-Asp-D-Tyr-Lys(N$^\epsilon$—CO—(CH$_2$)$_5$—NH—CO—CH=CH$_2$))
cyclo-(Arg-Gly-Asp-D-Phe-D-Lys(N$^\epsilon$—CO—(CH$_2$)$_5$—NH—CO—CH=CH$_2$))
cyclo-(Arg-Gly-Asp-D-Phe-Cys(S—CO—(CH$_2$)$_5$—NH—CO—CH=CH$_2$))
cyclo-(Arg-Gly-Asp-D-Phe-Dab(N$^\gamma$—CO—(CH$_2$)$_5$—NH—CO—CH=CH$_2$))
cyclo-(Arg-Gly-Asp-D-Trp-D-Cys(S—CO—(CH$_2$)$_5$—NH—CO—CH=CH$_2$))
cyclo-(Arg-Gly-Asp-D-Tyr-D-Cys(S—CO—(CH$_2$)$_5$—NH—CO—CH=CH$_2$))

cyclo-(Arg-Gly-Asp-Phe-D-Lys(N$^\epsilon$—CO—(CH$_2$)$_5$—NH—CO—CH=CH$_2$))
cyclo-(Arg-Gly-Asp-Trp-D-Lys(N$^\epsilon$—CO—(CH$_2$)$_5$—NH—CO—CH=CH$_2$))
cyclo-(Arg-Gly-Asp-Tyr-D-Lys(N$^\epsilon$—CO—(CH$_2$)$_5$—NH—CO—CH=CH$_2$))
cyclo-(Arg-Gly-Asp-Phe-D-Cys(S—CO—CH$_2$CH$_2$CO—NH—CH$_2$CH$_2$—SH))
cyclo-(Arg-Gly-Asp-Phe-Dab(N$^\gamma$—CO—(CH$_2$)$_5$—NH—CO—CH=CH$_2$))
cyclo-(Arg-Gly-Asp-Trp-D-Cys(S—CO—(CH$_2$)$_5$—NH—CO—CH=CH$_2$))
cyclo-(Arg-Gly-Asp-Tyr-D-Cys(S—CO—(CH$_2$)$_5$—NH—CO—CH=CH$_2$))
cyclo-(Arg-Gly-Asp-D-Trp-Orn(N$^\delta$—CO—(CH$_2$)$_5$—NH—CO—CH=CH$_2$))
cyclo-(Arg-Gly-Asp-D-Tyr-Orn(N$^\delta$—CO—(CH$_2$)$_5$—NH—CO—CH=CH$_2$))
cyclo-(Arg-Gly-Asp-D-Phe-Orn(N$^\delta$—CO—(CH$_2$)$_5$—NH—CO—CH=CH$_2$))
cyclo-(Arg-Gly-Asp-D-Trp-D-Orn(N$^\delta$—CO—(CH$_2$)$_5$—NH—CO—CH=CH$_2$))
cyclo-(Arg-Gly-Asp-D-Tyr-D-Orn(N$^\delta$—CO—(CH$_2$)$_5$—NH—CO—CH=CH$_2$))
cyclo-(Arg-Gly-Asp-D-Phe-D-Orn(N$^\delta$—CO—(CH$_2$)$_5$—NH—CO—CH=CH$_2$))
cyclo-(Arg-Gly-Asp-D-Trp-Dab(N$^\gamma$—CO—(CH$_2$)$_5$—NH—CO—CH=CH$_2$))
cyclo-(Arg-Gly-Asp-D-Tyr-Dab(N$^\gamma$—CO—(CH$_2$)$_5$—NH—CO—CH=CH$_2$))
cyclo-(Arg-Gly-Asp-D-Trp-Dap(N$^\beta$—CO—(CH$_2$)$_5$—NH—CO—CH=CH$_2$))
cyclo-(Arg-Gly-Asp-D-Tyr-Dap(N$^\beta$—CO—(CH$_2$)$_5$—NH—CO—CH=CH$_2$))
cyclo-(Arg-Gly-Asp-D-Phe-Dap(N$^\beta$—CO—(CH$_2$)$_5$—NH—CO—CH=CH$_2$))
cyclo-(Arg-Gly-Asp-D-Trp-D-Dap(N$^\beta$—CO—(CH$_2$)$_5$—NH—CO—CH=CH$_2$))
cyclo-(Arg-Gly-Asp-D-Tyr-D-Dap(N$^\beta$—CO—(CH$_2$)$_5$—NH—CO—CH=CH$_2$))
cyclo-(Arg-Gly-Asp-D-Phe-D-Dap(N$^\beta$—CO—(CH$_2$)$_5$—NH—CO—CH=CH$_2$)).

Example of Cell Adhesion Test

The adhesion of mouse MC3T3 H1 osteoblast cultures in vitro to RGD peptide-coated material surfaces was investigated. In the course of this, 50,000 cells/CM$^2$ were inoculated and, after incubation in serum-free medium at 37°/95% atmospheric humidity for one hour, the proportion of adherent cells was determined.

Cell adhesion rate [%]=adhered cells/inoculated cells ×100

Peptide: Cell Adhesion Rate [%]
cyclo-(Arg-Gly-Asp-D-Phe-Lys(N$^\epsilon$—CO—(CH$_2$)$_5$—NH—CO—CH=CH$_2$)): 11.3;
cyclo-(Arg-Gly-Asp-D-Phe-Lys(N$^\epsilon$—CO—(CH$_2$)$_5$—NH—CO—(CH$_2$)$_5$—NH—CO—CH=CH$_2$)): 92.4;
cyclo-(Arg-Gly-Asp-D-Phe-Lys(N$^\epsilon$—CO—CH$_2$—O—CH$_2$CH$_2$—O—CH$_2$CH$_2$—NH—CO—(CH$_2$)$_5$—NH—CO—CH=CH$_2$)): 109.0;
cyclo-(Arg-Gly-Asp-D-Phe-Lys(N$^\epsilon$—CO—CH$_2$CH$_2$CO—NH—CH$_2$CH$_2$—SH)): 86.2;
cyclo-(Arg-Gly-Asp-D-Phe-Lys(N$^\epsilon$—CO—CH$_2$—O—CH$_2$CH$_2$—O—CH$_2$CH$_2$—NH)$_2$—CO—(CH$_2$)$_5$—NH—CO—CH=CH$_2$)): 110.5.

What is claimed is:
1. A compound of the formula I

$$R—Q—X \qquad I$$

in which
R is cyclo-(Arg-Gly-Asp-Z), where Z is bonded via a side chain to Q, or if Q is absent, to X,
Q is absent, or is —(CO—R$^1$—NH—)$_m$, —(NH—R$^1$—CO—)$_m$, —(CO—R$^1$—CO—)$_m$, —(CO—CH$_2$—O—CH$_2$CH$_2$—O—CH$_2$CH$_2$—NH—)$_n$, —(NH—CH$_2$—O—CH$_2$CH$_2$—O—CH$_2$CH$_2$—CO—)$_n$, —(NH—CH$_2$CH$_2$—O—CH$_2$CH$_2$—O—CH$_2$—CO—)$_n$ or —(CO—CH$_2$—O—CH$_2$CH$_2$—O—CH$_2$CH$_2$—NH—)$_n$—(CO—R$^1$—NH—)$_m$,
X is —CO—CH=CH$_2$, —CO—C(CH$_3$)=CH$_2$, —NH—CH=CH$_2$, —NH—C(CH$_3$)=CH$_2$ or —NH—(CH$_2$)$_p$SR$^{10}$,
Z is in each case independently of one another an amino acid residue or a di- or tripeptide residue, where the amino acids independently of one another are selected from a group consisting of Ala, Asn, Asp, Arg, Cys, Gln, Glu, Gly, His, Homo-Phe, Ile, Leu, Lys, Met, Phe, Phg, Pro, Ser, Thr, Trp, Tyr, Val and M,
wherein said amino acids can be derivatized, and the amino acid residues are linked to one another in peptide fashion via the α-amino- and α-carboxyl groups, and
where M is always present,
M is a residue of NH(R$^8$)—CH(R$^3$)—COOH,
R$^1$ is absent or is R$^2$, R$^9$, R$^2$—R$^9$—R$^2$, or phenylene which is unsubstituted or mono- or disubstituted by R$^5$, where the chain length of R$^5$ is in each case independent of one another,
R$^2$ is alkylene having 1–10 C atoms, where 1 or 2 methylene groups can be replaced by S, —CH=CH— or —C≡C—,
R$^3$ is —R$^5$—R$^4$, —R$^6$—R$^4$ or —R$^7$—R$^4$,
R$^4$ is OH, NH$_2$, SH or COOH,
R$^5$ is alkylene having 1–6 C atoms,
R$^6$ is alkylenephenylene having 7–14 C atoms,
R$^7$ is alkylenephenylalkylene having 8–15 C atoms,
R$^8$ is H, A or alkylenephenyl having 7–12 C atoms,
R$^9$ is cycloalkylene having 3–7 C atoms,
R$^{10}$ is H or an S protective group,
A is alkyl having 1–6 C atoms,
Hal is F, Cl, Br or I
m and n in each case independently of one another are 0, 1, 2 or 3 and
p is 1,2, or 3,
where each optically active amino acid or amino acid derivative that is present is in either the D or L form; or
a salt thereof.
2. A compound according to claim 1 a) cyclo-(Arg-Gly-Asp-D-Phe-Lys(N$^\epsilon$—CO—CH$_2$CH$_2$CO—NH—CH$_2$CH$_2$—SH)) or a physiologically acceptable salt thereof;
b) cyclo-(Arg-Gly-Asp-D-Phe-Lys(N$^\epsilon$—CO—CH$_2$CH$_2$CO—NH—CH$_2$CH$_2$—SH)-Gly) or a physiologically acceptable salt thereof;
c) cyclo-(Arg-Gly-Asp-D-Phe-Lys(N$^\epsilon$—CO—(CH$_2$)$_5$—NH—CO—CH=CH$_2$)) or a physiologically acceptable salt thereof;
d) cyclo-(Arg-Gly-Asp-D-Phe-Lys(N$^\epsilon$—CO—(CH$_2$)$_5$—NH—CO—CH=CH$_2$)) or a physiologically acceptable salt thereof;

e) cyclo-(Arg-Gly-Asp-D-Phe-Lys(N$^\epsilon$—CO—CH$_2$—O—CH$_2$CH$_2$—O—CH$_2$CH$_2$—NH—CO—(CH$_2$)$_5$—NH—CO—CH=CH$_2$)) or a physiologically acceptable salt thereof; or f) cyclo-(Arg-Gly-Asp-D-Phe-Lys(N$^\epsilon$—(CO—CH$_2$—O—CH$_2$CH$_2$—O—CH$_2$CH$_2$—NH)$_2$—CO—(CH$_2$)$_5$—NH—CO—CH=CH$_2$)) or a physiologically acceptable salt thereof.

3. A compound according to claim 1, wherein R$^1$ is alkylene having 1–10 C atoms.

4. A compound according to claim 1, wherein Q is a 6-aminohexanoic acid radical, a succinyl radical, —(CO—CH$_2$—O—CH$_2$CH$_2$—O—CH$_2$CH$_2$—NH)—, —(CO—CH$_2$—O—CH$_2$CH$_2$—O—CH$_2$CH$_2$—NH—)CO—(CH$_2$)$_5$—NH—, —(CO—(CH$_2$)$_5$—NH)$_2$—, or —(CO—CH$_2$—O—CH$_2$CH$_2$—O—CH$_2$CH$_2$—NH—)$_2$CO—(CH$_2$)$_5$—NH—.

5. A compound according to claim 1, wherein M is Dap (diamino propionic acid), Ser, Cys, Asp, D-Asp, Dab (diamino butyric acid), homoserine, homocysteine, Glu, D-Glu, Thr, Orn, Lys, D-Lys, 4-aminomethyl-Phe or 4-aminomethyl-D-Phe.

6. A compound according to claim 1, wherein Z is M.

7. A compound according to claim 1, wherein —R$^6$—R$^4$ is 2, 3- or 4-hydroxybenzyl, 2-, 3- or 4-aminobenzyl, 2-, 3- or 4-mercaptobenzyl, 2-, 3- or 4-carboxybenzyl, 2-, 3- or 4-hydroxyphenethyl, 2-, 3- or 4-aminophenethyl, 2-, 3- or 4-mercaptophenethyl, or 2-, 3- or or 4-carboxyphenethyl.

8. A compound according to claim 1, wherein Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly.

9. A compound according to claim 1, wherein Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly and X is —CO—CH=CH$_2$, —NH—CH=CH$_2$, or —NH—(CH$_2$)$_p$—SH.

10. A compound according to claim 1, wherein

Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly and X is —CO—CH=CH$_2$ or —NH—(CH$_2$)$_p$—SH.

11. A compound according to claim 1, wherein

Z is D-Phe-M, Phe-M, D-Trp-M, Trp-M, D-Tyr-M, Tyr-M, D-Phg-M, Phg-M, D-homo-Phe-M, homo-Phe-M or D-Phe-Lys-Gly X is —CO—CH=CH$_2$, —NH—CH=CH$_2$ or —NH—(CH$_2$)$_p$—SH and R$^1$ is alkylene having 1–10 C atoms wherein 1 or 2 methylene groups can be replaced by S, —CH=CH— or —C≡C—.

12. A compound according to claim 1, wherein

R is cyclo-(Arg-Gly-Asp-D-Phe-M), and

X is —CO—CH=CH$_2$, —NH—CH=CH$_2$ or —NH—(CH$_2$)$_p$—SH.

13. A compound according to claim 1, wherein

R is cyclo-(Arg-Gly-Asp-D-Phe-M) or,

Q is —CO—(CH$_2$)$_5$—NH, —CO—(CH$_2$)$_2$—CO—, —CO—CH$_2$—O—CH$_2$CH$_2$—O—CH$_2$CH$_2$—NH—, —(CO—CH$_2$—O—CH$_2$CH$_2$—O—CH$_2$CH$_2$—NH—)$_2$—CO—(CH$_2$)$_5$—NH—, —(CO—CH$_2$—O—CH$_2$CH$_2$—O—CH$_2$CH$_2$—NH—)$_1$—CO—(CH$_2$)$_5$—NH— or —(CO—(CH$_2$)$_5$—NH)$_2$—,

X is —CO—CH=CH$_2$, —NH—CH=CH$_2$ or —NH—(CH$_2$)$_p$—SH, and

R$^1$ is alkylene having 1–10 C atoms wherein 1 or 2 methylene groups can be replaced by S, —CH=CH— or —C≡C—.

14. A compound according to claim 1 wherein

Z is D-Phe-Lys-Gly, and

X is —CO—CH=CH$_2$, —NH—CH=CH$_2$ or —NH—(CH$_2$)$_p$—SH.

15. A compound according to claim 14, wherein

Z is D-Phe-Lys-Gly,

Q is —CO—(CH$_2$)$_5$—NH, —CO—(CH$_2$)$_2$—CO—, —CO—CH$_2$—O—CH$_2$CH$_2$—O—CH$_2$CH$_2$—NH—, —(CO—CH$_2$—O—CH$_2$CH$_2$—O—CH$_2$CH$_2$—NH—)$_2$—CO—(CH$_2$)$_5$—NH—, —(CO—CH$_2$—O—CH$_2$CH$_2$—O—CH$_2$CH$_2$—NH—)$_1$—CO—(CH$_2$)$_5$—NH— or —(CO—(CH$_2$)$_5$—NH)$_2$—,

X is —CO—CH=CH$_2$, —NH—CH=CH$_2$ or —NH—(CH$_2$)$_p$—SH, and

R$^1$ is alkylene having 1–10 C atoms wherein 1 or 2 methylene groups can be replaced by S, —CH=CH— or —C≡C—.

16. A method of covalently bonding a compound to a biocompatible device having a surface, comprising reacting a compound of claim 1, said compound having a functional group, to said biocompatible device having a surface to form a covalent bond between said functional group and said biocompatible device having a surface.

17. A process according to claim 16, wherein the biocompatible surface is that of an implant.

18. A method of inhibiting binding of an Arg-Gly-Asp-containing peptide to an integrin comprising contacting a compound of claim 1 with an integrin for a time and under conditions effective to inhibit binding of an Arg-Gly-Asp-containing peptide to an integrin.

19. A process for promoting adhesion of integrin-bearing cells to the surface of an implant comprising:

a) covalently bonding a compound according to claim 1 to the surface of the implant to produce a surface-modified implant; and b) contacting the surface-modified implant with the integrin-bearing cells for a time and under conditions effective to promote adhesion of integrin-bearing cells to the surface of an implant.

20. A process for preparing a compound according to claim 1, wherein

Q is absent, or is [CO—R$^1$—NH]$_m$, —(CO—CH$_2$—O—CH$_2$CH$_2$—O—CH$_2$CH$_2$—NH—)$_n$ or —(CO—CH$_2$—O—CH$_2$CH$_2$—O—CH$_2$CH$_2$—NH—)$_n$—[CO—R$^1$—NH]$_m$ X is —CO—CH=CH$_2$ or —CO—C(CH$_3$)=CH$_2$, R is cyclo-(Arg-Gly-Asp-Z), where Z is bonded in the side chain to Q, or if Q is absent, to X, said process comprising:

a) reacting a compound of formula II with a compound of formula III for a time and under conditions effective to form a compound of formula I; wherein formula II is

R—H          II;

formula III is

L—Q—X III;

wherein

R is cyclo-(Arg-Gly-Asp-Z), where Z is bonded in the side chain to Q, or if Q is absent, to X, L is Cl, Br, I or a free or reactive functionally modified OH group Q is absent, or is —[CO—R$^1$—NH]$_m$, —(CO—CH$_2$—O—CH$_2$CH$_2$—O—CH$_2$CH$_2$—NH—)$_n$ or —(CO—CH$_2$—O—CH$_2$CH$_2$—O—CH$_2$CH$_2$—NH—)$_n$—[CO—R$^1$—NH]$_m$ X is —CO—CH=CH$_2$ or —CO—C(CH$_3$)=CH$_2$, and b) optionally, treating the compound of formula I with an acid or base to form a salt thereof; and c) optionally, isolating said compound of formula I or said salt thereof.

21. A process for preparing a compound according to claim 1, wherein

Q is absent, or is —[CO—R$^1$—NH]$_m$, —(CO—CH$_2$—O—CH$_2$CH$_2$—O—CH$_2$CH$_2$—NH—)$_n$ or —(CO—CH$_2$—O—CH$_2$CH$_2$—O—CH$_2$CH$_2$—NH—)$_n$—[CO—R$^1$—NH]$_m$ X is —CO—CH=CH$_2$ or —CO—C(CH$_3$)=CH$_2$, R is cyclo-(Arg-Gly-Asp-Z), where Z is bonded in the side chain to Q, or if Q is absent, to X, said process comprising a) reacting a compound of formula IV with a compound of formula V for a time and under conditions effective to form a compound of formula I; wherein formula IV is

R—Q—H      IV;

formula V is

L—X      V;

wherein

R is cyclo-(Arg-Gly-Asp-Z), where Z is bonded in the side chain to Q, or if Q is absent, to X, L is Cl, Br, I or a free or reactive functionally modified OH group Q is absent, or is —[CO—R$^1$—NH]$_m$, —(CO—CH$_2$—O—CH$_2$CH$_2$—O—CH$_2$CH$_2$—NH—)$_n$ or —(CO—CH$_2$—O—CH$_2$CH$_2$—O—CH$_2$CH$_2$—NH—)$_n$—[CO—R$^1$—NH]$_m$ X is —CO—CH=CH$_2$ or —CO—C(CH$_3$)=CH$_2$, and b) optionally, treating the compound of formula I with an acid or base to form a salt thereof; and c) optionally, isolating said compound of formula I or said salt thereof.

22. A process for preparing a compound according to claim 1, wherein

Q is absent, or is —[NH—R$^1$—CO—]$_m$, —[CO—R$^1$—CO]$_m$, —(NH—CH$_2$—O—CH$_2$CH$_2$—O—CH$_2$CH$_2$—CO—)$_n$ or —(NH—CH$_2$CH$_2$—O—CH$_2$CH$_2$—O—CH$_2$—CO—)$_n$ X is —NH—CH=CH$_2$ or —NH—C(CH$_3$)=CH$_2$, or —NH—(CH$_2$)$_p$—SR$^{10}$, R$^{10}$ is an S protective group R is cyclo-(Arg-Gly-Asp-Z), where Z is bonded in the side chain to Q, or if Q is absent, to X, said process comprising a) reacting a compound of formula IV with a compound of formula VII for a time and under conditions effective to form a compound of formula I; wherein formula IV is

R—L      IV;

formula VII is

H—Q—X      VII;

wherein

R is cyclo-(Arg-Gly-Asp-Z), where Z is bonded in the side chain to Q, or if Q is absent, to X, L is Cl, Br, I or a free or reactive functionally modified OH group Q is absent, or is —[NH—R$^1$—CO]$_m$, —(NH—CH$_2$—O—CH$_2$CH$_2$—O—CH$_2$CH$_2$—CO—)$_n$ or —(NH—CH$_2$CH2—O—CH$_2$CH$_2$—O—CH$_2$—CO—)$_n$, X is —NH—CH=CH$_2$ or —NH—C(CH$_3$)=CH$_2$, or —NH—(CH$_2$)$_p$—SR$^{10}$, R$^{10}$ is an S protective group, and b) optionally, treating the compound of formula I with an acid or base to form a salt thereof; and c) optionally, isolating said compound of formula I or said salt thereof.

23. A process for preparing a compound of according to claim 1, wherein

Q is absent, or is —[NH—R$^1$—CO—]$_m$, —[CO—R$^1$—CO]$_m$, —(NH—CH$_2$—O—CH$_2$CH$_2$—O—CH$_2$CH$_2$—CO—)$_n$ or —(NH—CH$_2$CH$_2$—O—CH$_2$CH$_2$—O—CH$_2$—CO—)$_n$ X is —NH—CH=CH$_2$ or —NH—C(CH$_3$)=CH$_2$, or —NH—(CH$_2$)$_p$—SR$^{10}$, R$^{10}$ is an S protective group R is cyclo-(Arg-Gly-Asp-Z), where Z is bonded in the side chain to Q, or if Q is absent, to X, said process comprising a) reacting a compound of formula VIII with a compound of formula IX for a time and under conditions effective to form a compound of formula I; wherein formula VIII is

R—Q—L      VIII;

formula IX is

H—X      IX;

wherein

R is cyclo-(Arg-Gly-Asp-Z), where Z is bonded in the side chain to Q, or if Q is absent, to X, L is Cl, Br, I or a free or reactive functionally modified OH group Q is absent, or is —[NH—R$^1$—CO]$_m$, —[CO—R$^1$—CO]$_m$, —(NH—CH$_2$—O—CH$_2$CH$_2$—O—CH$_2$CH$_2$—CO—)$_n$ or —(NH—CH$_2$CH2—O—CH$_2$CH$_2$—O—CH$_2$—CO—)$_n$, X is —NH—CH=CH$_2$ or —NH—C(CH$_3$)=CH$_2$, or —NH—(CH$_2$)$_p$—SR$^{10}$, R$^{10}$ is an S protective group, and b) optionally, treating the compound of formula I with an acid or base to form a salt thereof; and c) optionally, isolating said compound of formula I or said salt thereof.

24. A method of preparing a device which is useful as an implant to which is covalently bonded a compound according to claim 1, wherein at least part of the outside surface of the device is biocompatible, said method comprising:

a) reacting a compound according to claim 21 with an implant for a time and under conditions effective to form a covalent bond between substituent X and the surface of the device, wherein the outside surface of the device is biocompatible, and b) recovering the device of step (a).

\* \* \* \* \*

UNITED STATES PATENT AND TRADEMARK OFFICE
CERTIFICATE OF CORRECTION

PATENT NO.   : 6,610,826 B1
DATED        : August 26, 2003
INVENTOR(S)  : Joerg Meyer et al.

It is certified that error appears in the above-identified patent and that said Letters Patent is hereby corrected as shown below:

Column 20,
Line 47, reads "or is $[CO-R^1-NH]_m$," should read -- or is $-[CO-R^1-NH]_m$, --.

Column 22,
Line 60, reads "claim 21" should read -- claim 1 --.

Signed and Sealed this

Seventh Day of February, 2006

JON W. DUDAS
*Director of the United States Patent and Trademark Office*